US00PP25745P3

(12) United States Plant Patent
Bradford et al.

(10) Patent No.: US PP25,745 P3
(45) Date of Patent: Jul. 28, 2015

(54) PEACH TREE NAMED 'PEARL PRINCESS XII'

(50) Latin Name: *Prunus persica*
Varietal Denomination: Pearl Princess XII

(71) Applicants: Lowell Glen Bradford, Le Grand, CA (US); Jon Michael Quisenberry, Merced, CA (US)

(72) Inventors: Lowell Glen Bradford, Le Grand, CA (US); Jon Michael Quisenberry, Merced, CA (US)

( * ) Notice: Subject to any disclaimer, the term of this patent is extended or adjusted under 35 U.S.C. 154(b) by 84 days.

(21) Appl. No.: 13/998,853

(22) Filed: Dec. 16, 2013

(65) Prior Publication Data

US 2015/0173276 P1 Jun. 18, 2015

(51) Int. Cl.
*A01H 5/08* (2006.01)

(52) U.S. Cl.
USPC ..... Plt./196

(58) Field of Classification Search
USPC ..... Plt./196
CPC ..... A01H 5/0868; A01H 5/0837
See application file for complete search history.

(56) References Cited

U.S. PATENT DOCUMENTS

PP23,867 P3 9/2013 Bradford

*Primary Examiner* — Kent L Bell

(57) ABSTRACT

The present invention relates to a new and distinct variety of peach tree, *Prunus persica*, broadly characterized by a medium size, moderately vigorous, hardy, self-fertile, productive and regular bearing tree. The variety blooms during the mid to late blooming season and requires about 600 chilling hours. The fruit matures under the ecological conditions described in the last half of August, with first picking on Aug. 20, 2013. The fruit is uniform, very large in size, globose in shape, freestone in type, firm and melting in texture, white in flesh color, mostly red in skin color, and a tasty balance of light acid and sugar in flavor.

1 Drawing Sheet

Botanical classification: *Prunus persica.*
Variety denomination: 'Pearl Princess XII'.

BACKGROUND OF THE VARIETY

In a continuing effort to improve the quality of shipping fruits, we, the inventors, typically hybridize a large number of peach, nectarine, plum, apricot, and cherry seedlings each year. We also grow a smaller number of open pollinated seeds of each of these fruits, usually to capture recessive traits. The present invention relates to a new and distinct variety of peach tree, which has been denominated varietally as 'Pearl Princess XII'.

During the summer of 2006 we gathered about 1000 open pollinated seeds from the fruit of several different peach trees that exhibited desired characteristics. These trees, some experimental and some patented varieties, were all located on the breeding grounds of our experimental orchard located near Le Grand, Calif., in Merced County (San Joaquin Valley). All of the seeds that came from white flesh freestone peaches were mixed together and dried in a container labeled "WPF (OP)". These seeds were then planted as a group in November, 2006, in row "36M" of the experimental orchard referenced above. About 500 of the seed germinated and sprouted the following spring. The resulting group of seedlings were grown using normal cultural practices for three years, and then the fruit from each individual tree was carefully evaluated. During the fruit evaluation season of 2011 we selected the present variety as a single tree from the group of seedlings described above for exhibiting desirable qualities. Subsequent to origination of the present variety of peach tree, we asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is most similar to 'Glacier Princess' peach (U.S. Plant Pat. No. 23,867) by having a medium vigorous tree with large blossoms, by having reniform leaf glands, by being self-fertile, by having a bitter tasting kernel, and by producing white flesh freestone peaches that are very large in size, mostly red in skin color, globose in shape, firm in texture, and good in flavor, but is distinguished therefrom by blooming about ten days later, by requiring more chilling hours, and by producing fruit that matures about fifteen days earlier.

SUMMARY OF VARIETY

The present peach variety is characterized by a medium size, moderately vigorous, hardy, self-fertile, productive and regular bearing tree. The variety blooms during the mid to late blooming season and requires about 600 chilling hours. The fruit matures under the ecological conditions described in the last half of August, with first picking on Aug. 20, 2013. The fruit is uniform, very large in size, globose in shape, freestone in type, firm and melting in texture, white in flesh color, mostly red in skin color, and a tasty balance of light acid and sugar in flavor.

DRAWING

The accompanying photograph consists of four whole fruits positioned to display the characteristics of the skin color and form, one divided fruit to reveal the flesh and stone, two insets to reveal buds and blossoms, and typical leaves.

POMOLOGICAL CHARACTERISTICS

Referring now more specifically to the pomological characteristics of this new and distinct variety of peach tree, the following has been observed under the ecological conditions prevailing near Le Grand, Merced County (San Joaquin Valley), Calif., and was developed at the state of firm ripe on Aug. 23, 2013, on the original tree during its seventh growing season. The blossom and flower descriptions were made the previous blooming season. All major color code designations are by reference to the Inter-Society Color Council, National Bureau of Standards. Common color names are also used occasionally.

It is to be noted that the 2013 fruit season in California was very warm during the spring and the ripening times of almost all varieties were about ten days earlier than other years.

PARENTAGE

Seed parent: Unknown white flesh freestone peach.
Pollen parent: Unknown.

TREE

Size: Medium to large, reaching and maintaining a height of 10' [3.05 m.] and a spread of 9' [2.74 m.] after seven growing seasons utilizing typical dormant pruning.
Vigor: Medium vigor, responding typically to irrigation and fertilization. The variety grows about 3' [0.91 m.] of surplus top-growth during the spring and summer. The plant should be grown on a standard commercial rootstock for production purposes.
Growth: Spreading and dense.
Form: Vase type.
Hardiness: Hardy with respect to central California winters.
Heat tolerance: Observed to perform adequately in typical central California climatic conditions, which typically include extended periods of heat.
Drought tolerance: Variety is developed for commercial orchards and requires regular irrigation.
Production: Productive, thinning necessary.
Fertility: Self-fertile.
Bearing: Regular bearer with no alternate bearing yet observed.
Approximate chilling requirement: 600 hours.
Trunk:
- *Size.*—Stocky, reaching a maximum diameter of 4" [101.6 mm.] after the seventh growing season.
- *Texture.*—Medium shaggy.
- *Bark color.*—A Light grayish brown [60. l.gy.Br] and Dark grayish brown [62. d.gy.Br] variegation with Brownish orange [54. brO] crevices present.
- *Lenticels.*—Approximate Number Per Square Inch: 6. Color: Dark orange yellow [72. d.OY]. Average Size: ¼" [6.4 mm.]. Shape: Eye-shaped, elongated.

Branches:
- *Size.*—Diameter of main scaffold is 2¾" [69.9 mm.] measured 12" above the crotch, diameter of limb is 1¾" [44.5 mm.] measured 12" above the first fork.
- *Texture.*—Smooth on first and second year wood, increasing roughness with age.
- *Color.*—1st Year Wood Topside: Grayish red [19. gy.R]. 1st Year Wood Underside: Brilliant yellow green [116. brill.YG]. Older Wood: A Grayish brown [61. gy.Br] and Dark grayish brown [62. d.gy.Br] variegation with Light grayish yellowish brown [79. l.gy.yBr] crevices present.
- *Lenticels.*—Number Per Square Inch: About 50 on second year wood. Color: Light yellowish brown [76. l.yBr]. Size: 1/64" [0.4 mm.] to 1/16" [1.6 mm.] on second year wood. Shape: Eye-shaped, elongated.

Leaves:
- *Size.*—Large. Average Length: 6¼" [158.8 mm.]. Average Width: 1¾" [44.5 mm.].
- *Arrangement.*—Alternate.
- *Thickness.*—Medium.
- *Form.*—Elliptical.
- *Apex.*—Acuminate.
- *Base.*—Acute to rounded.
- *Surface.*—Smooth.
- *Color.*—Dorsal Surface: Deep yellow green [118. deep YG]. Ventral Surface: Moderate yellow green [120. m.YG].
- *Margin.*—Finely serrate.
- *Venation.*—Pinnately net veined.
- *Vein color.*—Light yellow green [119. l.YG].
- *Petiole.*—Average Length: 7/16" [11.1 mm.]. Average Thickness: 1/16" [1.6 mm.]. Color: Brilliant yellow green [116. brill.YG].
- *Stipules.*—Number: Usually 2 per leaf, up to 6 per growing tip. Average Length: ⅜" [9.5 mm.]. Color: Brilliant yellow green [116. brill.YG] becoming Dark grayish reddish brown [47. d.gy.rBr] with maturity.
- *Glands.*—Number: 2 to 6 per leaf. Position: Alternately positioned on base of blade with a few on petiole. Size: Medium. Form: Reniform. Color: Brilliant yellow green [116. brill.YG] acquiring a Deep reddish brown [41. deep rBr] center with age.
- *Leaf buds.*—Pointed, medium in size.

Flower buds:
- *Hardiness.*—Hardy, with respect to central California winters.
- *Diameter.*—Typically 5/16" [7.9 mm.] 1 week before bloom.
- *Length.*—Typically ⅝" [15.9 mm.] 1 week before bloom.
- *Form.*—Not appressed.
- *Surface.*—Pubescent.
- *Tip color.*—Light purplish pink [249. l.pPk].

Flowers: Perfect, complete, perigynous, usually a single pistil, about thirty stamens, five sepal and petal locations alternately positioned.
- *Type.*—Showy, large.
- *Average flower diameter.*—2" [50.8 mm.].
- *Number of petals.*—Usually five, extra petal fragments commonly occur, double blossoms rarely observed.
- *Petal shape.*—Circular to oval.
- *Petal margin.*—Entire, wavy, occasional notches.
- *Average petal diameter.*—¾" [19.1 mm.].
- *Average petal length.*—13/16" [20.6 mm.].
- *Petal apex.*—Rounded.
- *Petal base.*—Rounded to somewhat truncate.
- *Petal color.*—Light pink [4. l.Pk] toward the apex, Strong purplish pink [247. s.pPk] toward the base on both sides.
- *Anther color.*—Light yellowish pink [28. l.yPk] over a Light yellow [86. l.Y] center at bloom onset.
- *Stigma color.*—Light greenish yellow [101. l.gY].

*Average pistil length.*—13/16" [20.6 mm.].
*Average stamen length.*—5/8" [15.9 mm.].
*Sepal color.*—Dark purplish red [259. d.pR] on the outer surface.
*Sepal length.*—1/4" [6.4 mm.].
*Sepal width.*—3/16" [4.8 mm.].
*Sepal apex.*—Rounded to elliptical to match the sepal length and width.
*Fragrance.*—Moderate.
*Blooming period.*—Medium to late, five days before 'Diamond Princess' (U.S. Plant Pat. No. 7,066) peach.
*Onset of bloom.*—One percent on Mar. 7, 2013.
*Date of full bloom.*—Mar. 14, 2013.
*Duration of bloom.*—One to two weeks, dependent on ambient temperature.
*Number per cluster.*—1 to 3 with single flowers most common.

FRUIT

Maturity when described: Firm ripe, Aug. 23, 2013.
Date of first picking: Aug. 20, 2013.
Date of last picking: Aug. 30, 2013.
Size: Uniform, very large.
*Average diameter axially.*—3 1/8" [79.4 mm.].
*Average diameter across suture plane.*—3 5/16" [84.2 mm.].
*Average diameter across cheek plane.*—3 3/8" [85.7 mm.].
*Typical weight.*—11.4 ounces [323 grams].
Form: Uniform, globose, symmetrical.
*Longitudinal section form.*—Round to slightly oblate.
*Axial view.*—Round.
Suture: An inconspicuous line located in a shallow groove that extends from the base, along the side, to just beyond the pistil point.
*Near the base.*—A very shallow groove.
*Along the side.*—A line with some stitching.
*Near the apex.*—A shallow groove.
Ventral surface: Rounded, lipped slightly toward the apex on both sides.
Lips: Equal toward the apex, slightly unequal along the sides.
Cavity: Flaring, circular, suture showing on one side, Pinkish white [9. pkWhite] stem markings typical.
*Depth.*—3/4" [19.1 mm.].
*Breadth.*—1 7/16" [36.5 mm.].
Base: Somewhat truncate.
Apex: Rounded.
Pistil point: Apical, negligible in length, sometimes depressed within the suture.
Stem: Medium.
*Average length.*—3/8" [9.5 mm.].
*Average width.*—3/16" [4.8 mm.].
Skin:
*Thickness.*—Medium.
*Surface.*—Pubescent.
*Tenacity.*—Tenacious to flesh.
*Astringency.*—Non-astringent.
*Tendency to crack.*—None observed in dry season.
*Color.*—Dark red [16. d.R] smoothly blending to Light grayish red [18. l.gy.R] with Yellowish white [92. yWhite] areas where protected from the sun.
*Down.*—Moderate, short, does not roll up when rubbed.
Flesh:
*Color.*—Mostly White [263. White] with Pinkish white [9. pkWhite] and Moderate red [15. m.R] streaking toward the stone.
*Surface of pit cavity.*—Covered with Dark red [16. d.R] fibers.
*Amygdalin.*—Slight.
*Juice.*—Moderate, rich.
*Texture.*—Firm, crisp, melting.
*Fibers.*—Abundant, tender.
*Ripens.*—Somewhat earlier toward the apex.
*Flavor.*—A delicious balance of slight acid and strong sugar, typically 16 to 18 brix.
*Aroma.*—Very slight.
*Eating quality.*—Very good.

STONE

Type: Freestone.
Form: Oval.
Hilum: Narrow.
Base: Rounded to truncate.
Apex: Acuminate.
Sides: Fairly equal.
Surface: Irregularly furrowed toward the apex, pitted toward the base.
Ridges: Jagged.
External color: Moderate brown [58. m.Br].
Pit wall color when cracked: Moderate brown [58. m.Br].
Cavity surface color: Strong yellowish brown [74. s.yBr].
Average pit wall thickness: 1/4" [6.4 mm.]
Average width: 1 1/8" [28.6 mm.].
Average length: 1 5/8" [41.3 mm.].
Average breadth: 13/16" [20.6 mm.].
Tendency to split: Very slight.
Kernel:
*Form.*—Oval.
*Skin color.*—Strong yellowish brown [74. s.yBr] when first removed.
*Pellicle color.*—Grayish brown [61. gy.Br].
*Vein color.*—Grayish brown [61. gy.Br].
*Taste.*—Bitter.
*Viable.*—Yes.
*Average width.*—7/16" [11.1 mm.].
*Average length.*—3/4" [19.1 mm.].
*Amygdalin.*—Abundant.

USE

Market: Fresh market and long distance shipping.
Keeping quality: Good, fruit quality observed to remain in good condition after 17 days in standard cold room at 36° Fahrenheit [2° Celsius].
Shipping quality: Good.
Resistance to insects: No unusual susceptibilities noted.
Resistance to diseases: No unusual susceptibilities noted.

OTHER NOTES

Although the new variety of peach tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of peach tree, substantially as illustrated and described, that is most similar to 'Glacier Princess' peach (U.S. Plant Pat. No. 23,867) by having a medium vigorous tree with large blossoms, by having reniform leaf glands, by being self-fertile, by having a bitter tasting kernel, and by producing white flesh freestone peaches that are very large in size, mostly red in skin color, globose in shape, firm in texture, and good in flavor, but is distinguished therefrom by blooming about ten days later, by requiring more chilling hours, and by producing fruit that matures about fifteen days earlier.

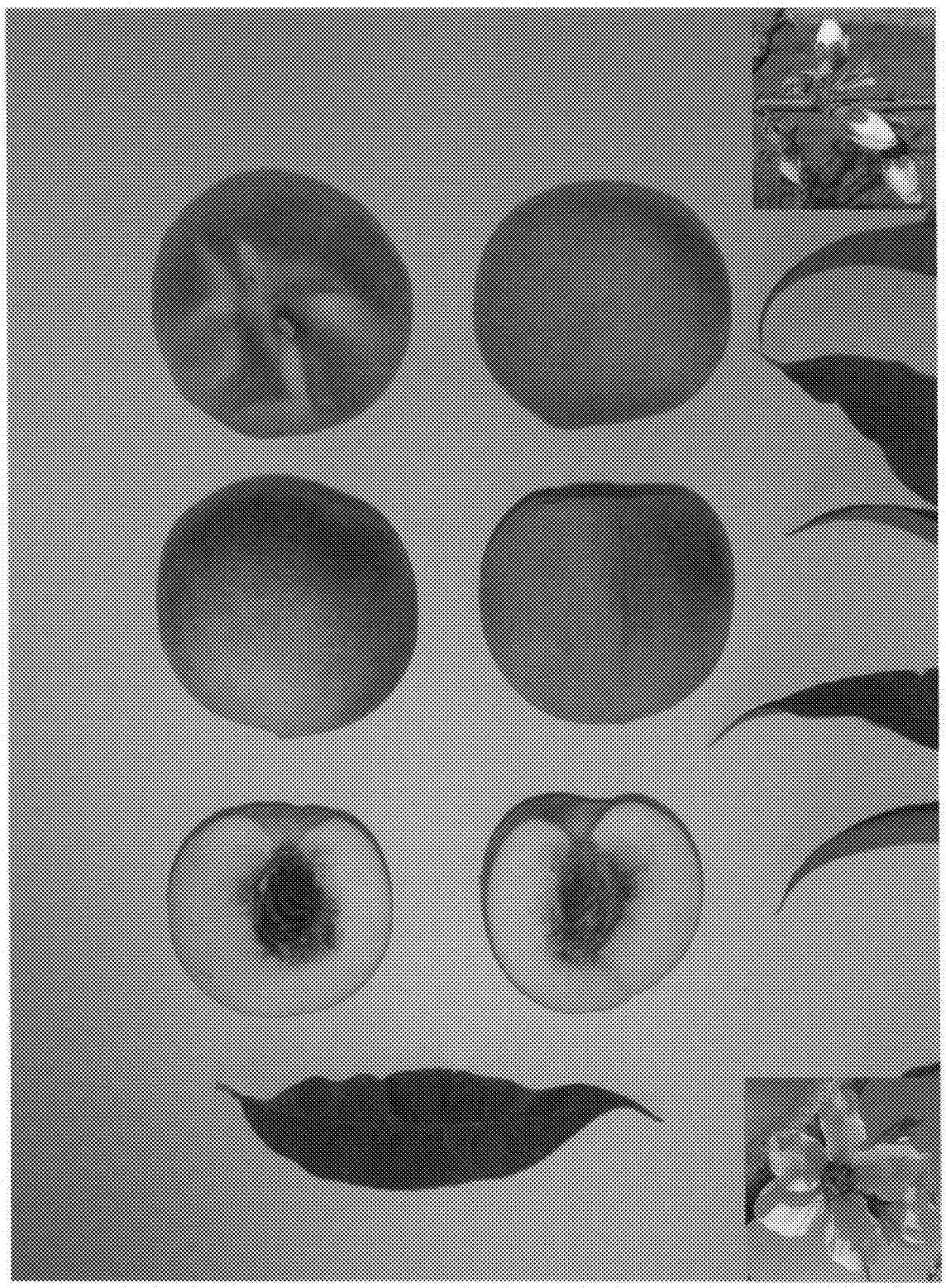

* * * * *